US006355793B1

(12) United States Patent
Lin

(10) Patent No.: US 6,355,793 B1
(45) Date of Patent: Mar. 12, 2002

(54) ORGANOMETALLIC ZEOLITE

(75) Inventor: Kuan-Jiuh Lin, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 09/342,304

(22) Filed: Jun. 29, 1999

(51) Int. Cl.$^7$ ............................................... C07B 47/00
(52) U.S. Cl. ....................................................... 540/145
(58) Field of Search ......................................... 540/145

(56) References Cited

PUBLICATIONS

Abrahams et al., "Assembly of Porphyrin Building Blocks into Network Structures With Large Channels", Nature 369:727–729, 1994.
Freyhardt et al., "A High–silica Zeolite with a 14–Tetrahedral–atom Pore Opening", Nature 381:295–298, 1996.
Janiak, "Functional Organic Analogues of Zeolites Based on Metal–Organic Coordination Frameworks", Angew, Chem. Int. Ed. Engl. 36:1431–1434, 1997.
Jones et al., "Organic–functionalized Molecular Sieves as Shape–selective Catalysts", Nature 393:52–54, 1998.
Kresge et al., "Ordered Mesoporous Molecular Sieves Synthesized by a Liquid–crystal Template Mechanism", Nature 359:710–712, 1992.
Yaghi et al., "Selective Binding and Removal of Guests in a Microporous Metal–Organic Framework", Nature 378:703–706, 1995.

Primary Examiner—Richard L. Raymond
(74) Attorney, Agent, or Firm—Fish & Richardson P.C.

(57) ABSTRACT

The invention relates to an organometallic zeolite which is formed of a multiplicity of units, each of which is of the formula $(X.M)_m$, wherein M is a metal ion selected from the group consisting of $Ni^{2+}$, $Sn^{2+}$, $Mg^{2+}$, $Ca^{2+}$, $Fe^{2+}$, $Co^{2+}$, $Mn^{2+}$, and $Ru^{2+}$; X is a porphine which coordinates to a metal ion to form an (X.M) and is substituted with at least two linking groups and optionally with one or more non-linking groups; and m is an integer ranging from 4 to 12. Each linking group is an oxygen-, nitrogen-, or sulfur-containing moiety, and each of the non-linking groups, independently, is aryl, heteroaryl, aralkyl, or heteroaralkyl, optionally substituted with alkyl, alkoxy, hydroxyl, hydroxylalkyl, carboxyl, halo, haloalkyl, amino, aminoalkyl, mercapto, mercaptoalkyl, alkylcarbonyloxy, alkyloxycarbonyl, alkylcarbonyl, alkylcarbonylamino, aminocarbonyl, alkylsulfonylamino, aminosulfonyl, dihydroxyboryl, sulfo, or alkylsulfonyl. The organometallic zeolite can be used as molecular sieves, sorbents, or ion exchange materials.

18 Claims, 2 Drawing Sheets

ORGANOMETALLIC ZEOLITE

BACKGROUND OF THE INVENTION

Inorganic microporous solids such as zeolite (i.e., aluminosilicates) are particularly suitable to be used as molecular sieves, sorbents, or ion exchange materials because of their rigidity, stability, and large internal surface area. Organometallic analogs of zeolite can be tailor-made so as to confer properties not available in their inorganic counterparts, thereby expanding their applications as catalysts or components of biosensors. However, organometallic zeolite is generally fragile and heat-unstable. Thus, there exists a need for a robust organometallic zeolite with desired properties.

SUMMARY OF THE INVENTION

An aspect of this invention relates to an organometallic zeolite formed of a multiplicity of units, each of which is of formula (I):

$$(X.M)_m \qquad\qquad (I)$$

M is a metal ion (e.g., $Co^{2+}$ or $Mn^{2+}$). X is a cyclic ligand (e.g., porphine or phthalocyanine) which coordinates to the metal ion to form an X.M and is substituted with at least two linking groups (e.g., 4-pyridyl) and optionally with one or more non-linking groups (e.g., 4-pyridyl or phenyl). Each linking group contains a lone pair of electrons for coordination to a metal ion. Each of the non-linking groups, independently, is aryl, heteroaryl, aralkyl, or heteroaralkyl, optionally substituted with alkyl, alkoxy, hydroxyl, hydroxylalkyl, carboxyl, halo, haloalkyl, amino, aminoalkyl, thio, thioalkyl, alkylcarbonyloxy, alkyloxycarbonyl, alkylcarbonyl, alkylcarbonylamino, aminocarbonyl, alkylsulfonylamino, aminosulfonyl, boronic acid, sulfonic acid, or alkylsulfonyl. m is an integer which ranges from 4 to 12. The zeolite of this invention also has the following features: (1) each $(X.M)_m$ forms a ring-shaped structure with a pore of an interior diameter of 10 to 25 Å; (2) the non-linking group of each X.M, if present, is located inside a pore; (3) the linking group of each X.M coordinates to the metal ion of a neighboring X.M and the metal ion of each X.M further coordinates to a linking group of a neighboring X.M; and (4) each $(X.M)_m$ shares an X.M with each of its neighboring $(X.M)_m$.

Note that the just-described network of $(X.M)_m$ is a layer. A multiplicity of such layers stack together to form a zeolite of this invention. The pores of each layer are aligned to form channels perpendicular to the plane of the layers.

A salt of the above-described zeolite is also within the scope of this invention. For example, a salt can be formed between a negatively charged substituent of a non-linking group of X.M (e.g., carboxyl) and an alkali metal ion (e.g., a sodium ion or a potassium ion); an alkaline earth metal ion (e.g., a magnesium ion or a calcium ion); an ammonium ion ($NH_4^+$); or an organic ammonium group (e.g., tetramethylammonium ion or diisopropylethylammonium ion). As another example, if an amino group is present on a non-linking group, it can form a salt with a negatively charged counterion. Suitable counterions include, but are not limited to, chloride, hydrochloride, bromide, iodide, sulfate, nitrate, phosphate, or acetate.

Set forth below are some examples of X.M: cobalt(II) 5,10,15,20-tetra(4-pyridyl)-21H,23H-porphine; manganese (II) 5,15-di(4-pyridyl)-10,20-di(4-aminophenyl)-21H,23H-porphyrin, and manganese(II) (5,15-di(4-pyridyl)-10,20-di(4-hydroxyphenyl)-21H,23H-porphyrin).

As used herein, alkyl is a straight or branched hydrocarbon chain containing 1 to 8 carbon atoms. Examples of alkyl include, but are not limited to, methyl, ethyl, propyl, isopropyl, butyl, isobutyl, sec-butyl, tert-butyl, n-pentyl, 2-methylhexyl, and n-octyl.

By cycloalkyl is meant a cyclic alkyl group containing 3 to 8 carbon atoms. Some examples of cycloalkyl are cyclopropyl, cyclopentyl, cyclohexyl, cycloheptyl, adamantyl, and norbornyl. Heterocycloalkyl is a cycloalkyl group containing 1–3 heteroatoms such as nitrogen, oxygen, or sulfur. Examples of heterocycloalkyl include piperidinyl, piperazinyl, tetrahydropyranyl, tetrahydrofuryl, and morpholinyl.

Aryl is an aromatic group containing 6–12 ring atoms and can contain fused rings, which may be saturated, unsaturated, or aromatic. Examples of an aryl group include phenyl, naphthyl, biphenyl, phenanthryl, and anthracyl. Heteroaryl is aryl containing 1–3 heteroatoms such as nitrogen, oxygen, or sulfur and can contain fused rings. Some examples of heteroaryl are pyridyl, furanyl, pyrrolyl, thienyl, thiazolyl, oxazolyl, imidazolyl, indolyl, benzofuranyl, and benzthiazolyl.

Aralkyl refers to a moiety which contains both an alkyl group and an aryl group. By the same token, heteroaralkyl refers to a moiety containing both an alkyl group and a heteroaryl group.

Note that an amino group can be unsubstituted, mono-substituted, or di-substituted. It can be substituted with groups such as alkyl, cycloalkyl, heterocycloalkyl, aryl, heteroaryl, aralkyl, or heteroaralkyl. Halo refers to fluoro, chloro, bromo, or iodo.

Other features or advantages of the present invention will be apparent from the following detailed description of several embodiments, and also from the appending claims.

DETAILED DESCRIPTION OF THE INVENTION

An organometallic zeolite of this invention is formed of a multiplicity of building blocks, X.M, where X is a cyclic ligand and M is a metal ion. The cyclic ligand contains at least two linking groups and optionally contains a non-linking group. One example of a cyclic ligand is porphine. Porphine is a conjugated cyclic structure of four pyrrole rings linked together through 2- and 5-methine bridges. Porphine ligands can be prepared by condensing porphyrinogens or polypyrrolyl intermediates. See, e.g., U.S. Pat. No. 5,856,515. The linking group of porphine bridges a building block (i.e., porphine:M) to another building block. One example of a linking group is 4-pyridyl. The optional non-linking group can possess functional groups such as amino, hydroxyl, or carboxyl. Examples of non-linking groups include pyridyl, aminophenyl, and hydroxyphenyl. Non-linking groups and linking groups of a porphine ligand can be attached to the pyrrolyl rings or the methine bridges. The number of linking groups per porphine ranges from 2 to 4, and the number of non-linking groups, if present, ranges from 1 to 10. Some examples of porphine are 5,10,15,20- tetra(4-pyridyl)-21H,23H-porphine ("tpyp"), 5,15-di(4-pyridyl)-10,20-di(4-aminophenyl)-21H,23H-porphyrin ("trans-py$_2$p-NH$_2$"), and (5,15-di(4-pyridyl)-10,20-di(4-hydroxyphenyl)-21H,23H-porphyrin) ("trans-py$_2$p-OH").

Any metal ion that can coordinate octahedrally can be used to form the porphine:M building block. Examples of such metal ions include $Ni^{2+}$, $Sn^{2+}$, $Mg^{2+}$, $Ca^{2+}$, $Fe^{2+}$, $Co^{2+}$, $Mn^{2+}$, and $Ru^{2+}$.

The X.M building blocks can form a zeolite of this invention under hydrothermal conditions. For convenience, porphine is again used as an example. The following scheme illustrates the preparation of SMTP-1:M, a zeolite built with porphine:M building blocks. In this preparation, formation of building blocks and their networking to form a zeolite take place in one step. Specifically, an aqueous solution of porphine (e.g., tpyp or trans-py$_2$p-X) and a metal salt (e.g., CoCl$_2$) is heated to about 150 to 230° C. at about 700 to 1,900 psi so that the building blocks can form and associate with each other, and then slowly cooled to yield a crystalline zeolite product. See Examples 1–3 below. Methods such as X-ray diffraction, thermogravimetric analysis, and nitrogen adsorption-desorption can be used to characterize the product. See Examples 4–6 below.

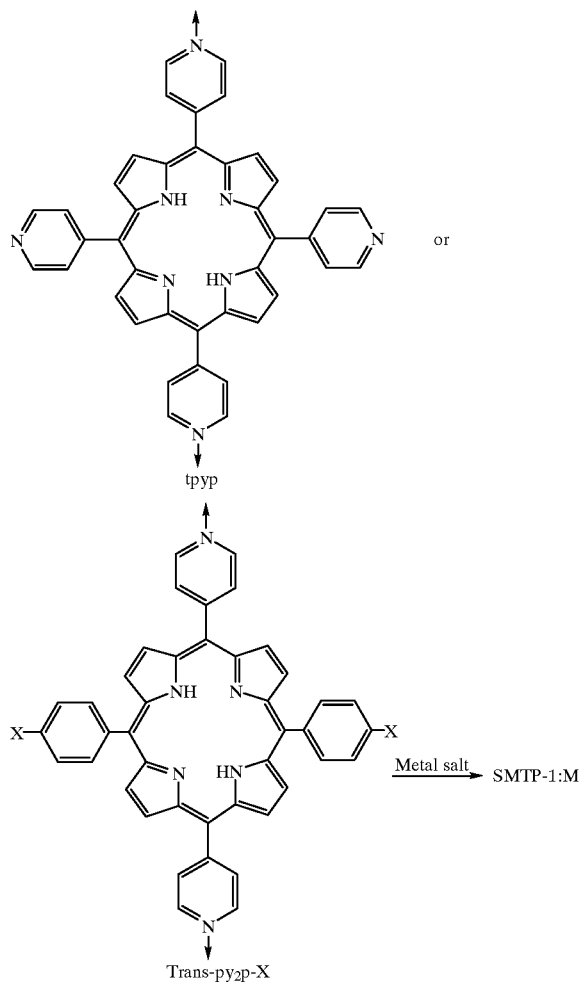

Figure 1:
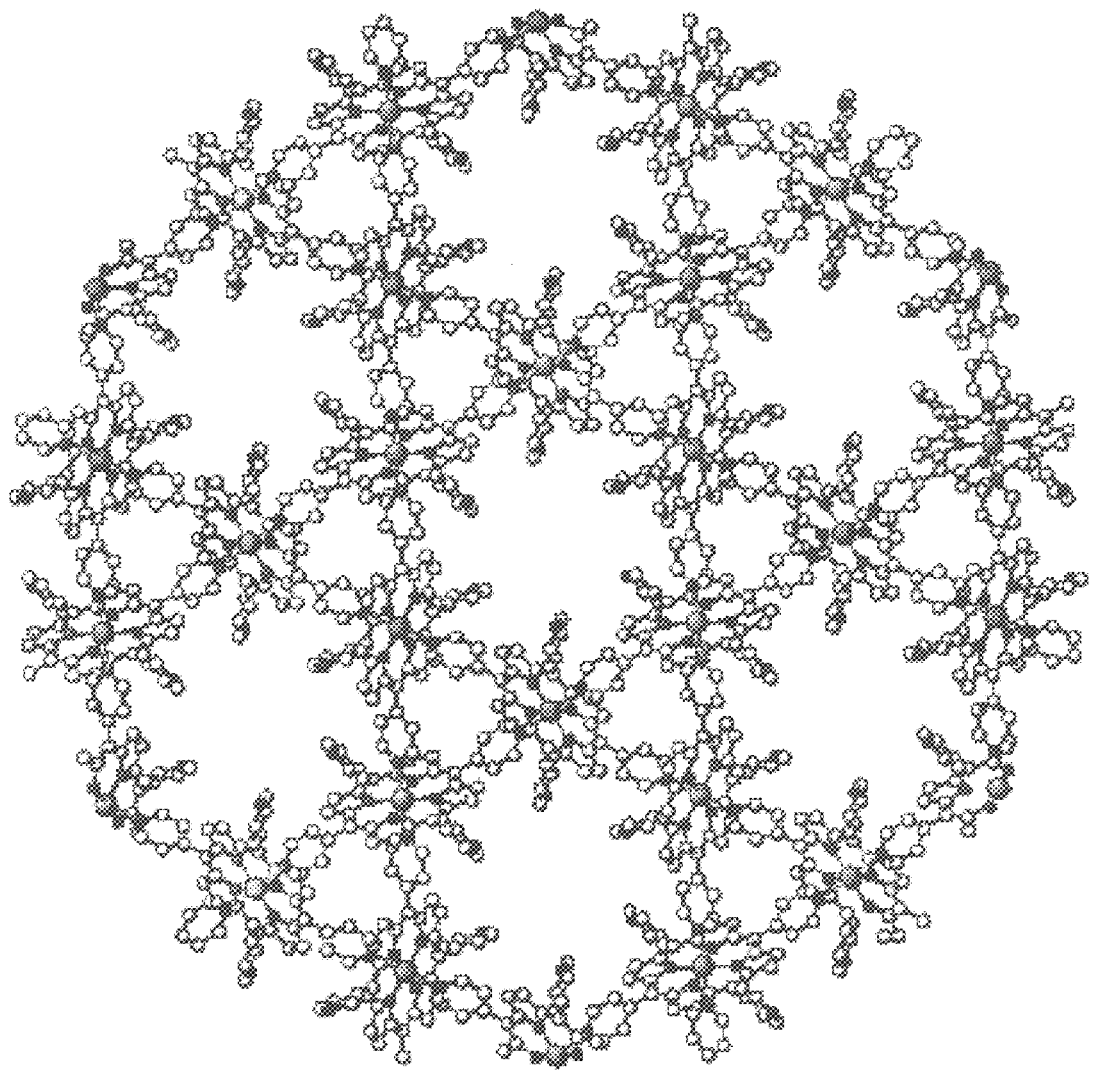
FIG. 1 is a section of a single layer of an SMTP-1:M crystal of this invention (SMTP-1:M stands for Supramolecular Materials prepared in Taiwan, Porphyrin-1:Metal ion). Hydrogen atoms and solvent molecules are omitted for clarity.
Figure 2:
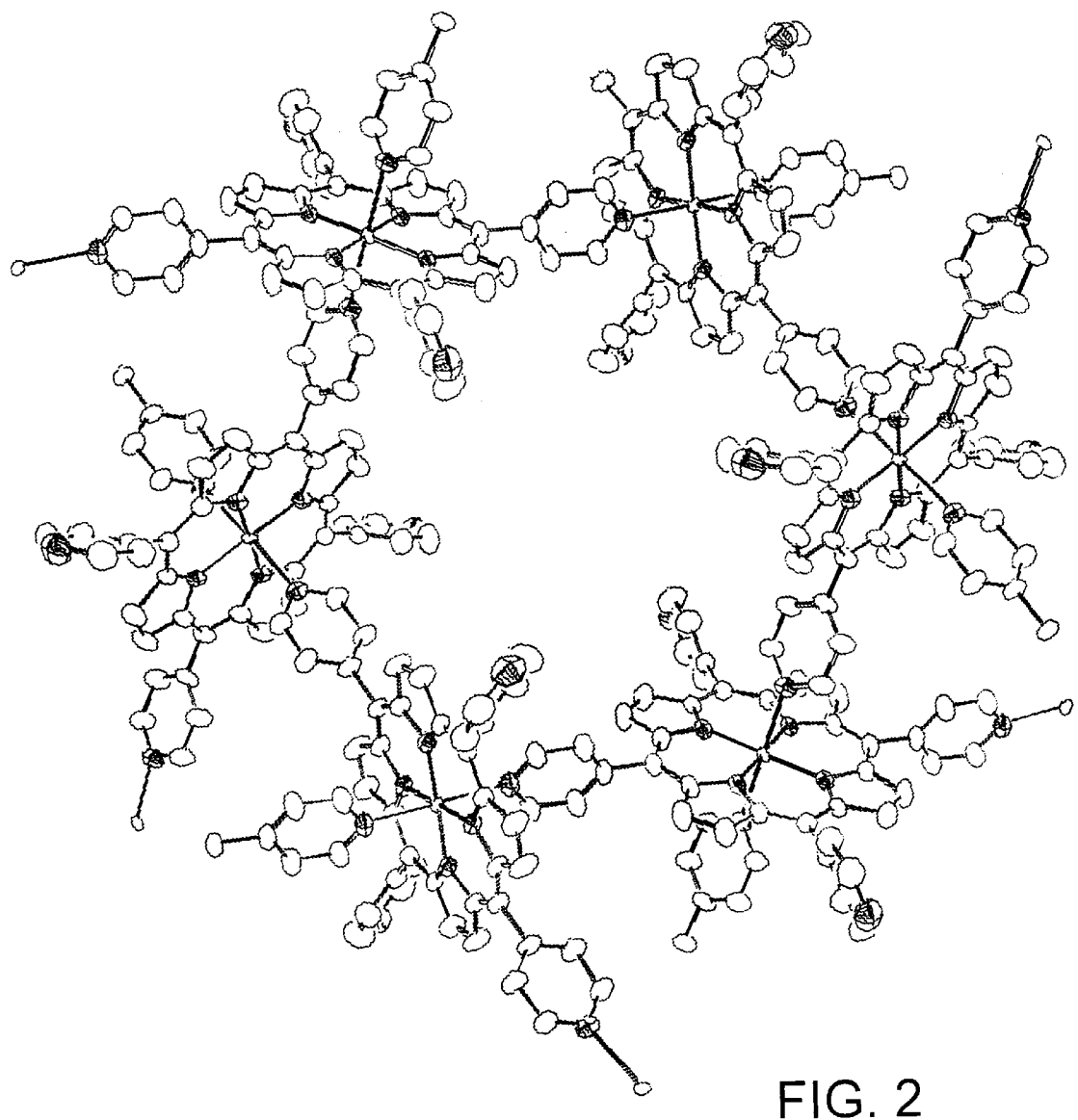
FIG. 2 is a single ring-shaped structure which is a unit of the SMTP-1:M layer shown in FIG. 1.

A zeolite prepared by the method described above which is made of porphine:M building blocks contains multiple layers, each of which having a number of ring-shaped structures formed from joining together 6 units of porphine:M. See FIG. 1 which shows a section of a single layer of an SMTP-1:M zeolite formed from a plurality of porphine:M (more specifically, tpyp:M) building blocks. A metal ion is located in the center of tpyp and coordinates to all four pyrrolyl nitrogen ring atoms of tpyp. The 5- and 15-pyridyl groups are the linking groups, each of which bonds to a metal ion of a neighboring tpyp:M axially. This metal ion, in turn, bonds to a linking group of another neighboring tpyp:M. Such arrangement links 6 tpyp:M building blocks to from a ring-shaped structure. See FIG. 2 which focuses on a single ring-shaped structure of such an SMTP-1:M crystal.

Note that each of the X.M building blocks has two non-linking groups, each of which is located inside the pore of the ring-shaped structure. Using the zeolite layer shown in FIG. 1 as an example, each tpyp:M building block is shared between two neighboring ring-shaped structures, thus interconnecting all the ring-shaped structures on the same layer. Further, each porphine ring within a layer aligns with a porphine ring of the two layers immediately above and below it so as to maximize overlapping of its π-orbitals. As a result, adjacent layers associate with each other via non-covalent π-π interactions so that the pores of the ring-shaped structures are aligned and run perpendicular to the plane of the layers to form a channel. Such channels restrict the size of molecules passing through the tpyp:M zeolite, thereby functioning as a molecular sieve.

As mentioned above, each of the non-linking groups is located inside the pores. Thus, any functionalities on the non-linking groups are also inside the pores and can contact with molecules that pass through the pores, thereby influencing the path of the molecules or even react with them. For example, in a hydrocarbon oxidation reaction where the primary products are polar molecules (alcohols, aldehydes, and ketones), selectivity of the reaction can be improved by using a tpyp:M zeolite with hydrophobic non-linking groups to facilitate separation of the hydrophobic reactants from the hydrophilic oxidation products. As another example, a tpyp:M zeolite with hydrophilic non-linking groups, e.g., amino, carboxyl, or hydroxyl, can selectively bind to molecules in the pores, functioning as a biological receptor or sensor.

In the following examples, zeolites of this invention were prepared and characterized by using X-ray diffraction, thermogravimetric analysis, and nitrogen adsorption-desorption isotherms.

Without further elaboration, it is believed that one skilled in the art can, based on the description herein, utilize the present invention to its fullest extent. The following specific examples, which described syntheses and characterization of zeolites of this invention, are therefore, to be construed as merely illustrative, and not limitative of the remainder of the disclosure in any way whatsoever. All publications recited herein, including patents, are hereby incorporated by reference in their entirety.

EXAMPLE 1

Preparation of a zeolite of formula (I) ("SMTP-1:Co") using cobalt(II) 5,10,15,20-tetra(4-pyridyl)-21H,23H-porphine as a building block A reaction mixture of CoCl$_2$.2H$_2$O (0.24 g), tpyp (0.12 g), CsOH (0.3 mL, w/w 50%), CH$_3$COOH (4 mL), and H$_2$O (4 mL) was sealed in a 23 mL Teflon-lined stainless autoclave, heated at 200° C. for 48 hours, and cooled to 70° C. at a rate of −9° C./hour. Needle-shaped purple crystals were then filtered off and washed with methanol. The yield of crystalline material was 85% (0.14 g) based on tpyp, and the synthesis was highly reproducible. Anal. Calcd: C, 63.54; N, 13.48; H, 3.88; found: C, 63.98; N, 14.93; H, 4.08. Monophase crystalline material was confirmed by X-ray powder diffraction. See Example 4 below.

EXAMPLE 2

Preparation of a zeolite of formula (I) ("SMTP-1:Mn(1)") using manganese (II) 5,10,15,20-tetra(4-pyridyl)-21H,23H-porphine as a building block A reaction mixture of $MnCl_2 \cdot 2H_2O$ (0.17 g), tpyp (0.12), CsOH (0.3 mL, 50% w/w), and $H_2O$ (10 mL) was sealed in a 23 mL Teflon-lined stainless autoclave. The mixture was heated to 200° C. and maintained at the same temperature for 48 hours, and cooled to 70° C. at a rate of −9° C./hour. Needle-shaped purple crystals (yield=5%) were obtained. Anal. Calcd: C, 56.41; N, 13.16; H, 7.10; found: C, 56.97; N, 13.20; H, 3.26. The structure was confirmed by X-ray diffraction. See Example 4 below.

EXAMPLE 3

Preparation of a zeolite of formula (I) ("SMTP-1:Mn (2)") using manganese (II) 5,10,15,20-tetra(4-pyridyl)-21H,23H-porphine as a building block A reaction mixture of $MnCl_2 \cdot 2H_2O$ (0.084 g), tpyp (0.12 g), CsOH (0.3 mL; 50% w/w), $C_2H_5OH$ (4 mL), and $H_2O$ (4 mL) was sealed in a 23 mL Teflon-lined stainless autoclave, heated at 200° C. for 48 hours, and cooled to 70° C. at a rate of −9° C./hour. Needle-shaped purple crystals were filtered off and washed with methanol. The yield of crystalline material was 86% (0.14 g) based on tpyp. Anal. Calcd: C, 63.54; N, 13.48; H, 3.88; found: C, 63.98; N, 14.93; H, 4.08. Monophase crystalline material was confirmed by X-ray powder diffraction. See Example 4 below.

EXAMPLE 4

X-ray Diffraction Studies

The zeolites prepared in Examples 1–3 above were characterized by X-ray diffraction using Siemens SMRAT-CCD (charge-coupled device) diffractometer where $\lambda(Mo, k\alpha) = 0.7107$ Å. Programs for computing structure solution and structure refinement used were HSELXTL PLUS and SHELXL-93, respectively. Reflections were refined based on $F^2$ by full matrix least squares. The highly disorder solvent, G, were not be completely located in the structure analysis. The homogeneity of crystalline products was confirmed by comparing the observed and calculated powder patterns derived from single crystal structure analysis. The crystallographic data of the three zeolites are listed below in Table 1.

TABLE 1

|  | SMTP-1:Co | SMTP-1:Mn(1) | SMTP-1:Mn(2) |
| --- | --- | --- | --- |
| Formula of $(X \cdot M)_m$ | $(Co:tpyp)_6:G$<br>$G = 12 CH_3COOH;$<br>$12 H_2O$ | $(Mn:tpyp)_6:G$<br>$G = 60 H_2O$ | $(Mn:tpyp)_6:G$<br>$G = 12 C_2H_5OH$<br>$24 H_2O$ |
| Crystal system<br>Space Group |  | Trigonal<br>R3 (No. 148) |  |
| Cell parameters | a = b = 23.7432(3)Å<br>c = 9.3124(2)Å<br>α = β = 90°<br>γ = 120° | a = b = 23.7624(2)Å<br>c = 9.3410(2)Å<br>α = β = 90°<br>γ = 120° | a = b = 33.3099(2)Å<br>c = 9.3306(2)Å<br>α = β = 90°<br>γ = 120° |
| Volume | 8645.9(2)Å$^3$ | 8683.1(1)Å$^3$ | 8965.8(2)Å$^3$ |
| Z | 3/2 | 3/2 | 3/2 |
| No. of reflections collected | 13474 | 17848 | 15211 |
| No. of reflections refined | 3397 | 3407 | 3533 |
| No. of parameters | 233 | 233 | 234 |
| Agreement factor ($R_1$) | 0.094 | 0.074 | 0.063 |
| Highest peak in final difference map | 1.539eÅ$^{-3}$ | 1.156eÅ$^{-3}$ | 0.413eÅ$^{-3}$ |
| Goodness of fit | 1.155 | 1.073 | 1.094 |

Each metal center was found to have a local symmetry of 1, and was coordinated octahedrally to four nitrogen atoms of the porphine. Average bond lengths for M-N (pyrrolyl nitrogen) in SMTP-1:Co, SMTP-1:Mn(1), and SMTP-1:Mn (2) were 1.994(5) Å; 1.992(4) Å, and 2.097(3) Å, respectively. Average bond lengths for M-N (trans pyridyl nitrogen) in SMTP-1:Co, SMTP-1:Mn(1), and SMTP-1:Mn (2) were 2.292(5) Å, 2.294(5) Å, and 2.411(3) Å, respectively. The tpyp building block was engaged in a trans-$\mu_{1,3}$ coordination mode. As is common in 5,10,15,20-tetraaryl porphyrins, large dihedral angles between the planes of pyridine rings and the porphyrin are observed (110° for pyridines which were linking groups and 68° for pyridines which were non-linking groups). SMTP-1 crystallized in the rhombohedral space R3 and therefore had a crystallographic 3 position. This represented the maximum $S_6$ point group symmetry that can be sustained by $(tpyp:M)_6$.

EXAMPLE 5

Thermogravimetric Analysis 8.5 mg of SMTP-1:Co was heated in air from 30° C. to 700° C. at a rate of 10° C./minute. Changes in weight % were recorded by Perkin-Elmer TGA 7.

Data obtained from thermogravimetric analysis revealed that the guest molecules were all liberated below 200° C., and the crystal lattice was thermally stable up to 380° C.

EXAMPLE 6

Nitrogen Adsorption-desorption Experiment

The pore size and surface area per gram of SMTP-1:Co was calculated by determining the number of moles of nitrogen gas adsorbed or desorbed using the BET theory. The experiment was performed using a Micrometric ASAP 2000 apparatus. Results obtained were summarized below in Table 2.

TABLE 2

| | |
|---|---|
| Single Point Surface Area at $P/P_o$ (relative pressure) = 0.204 | 116.3286 $m^2/g$ |
| BET Surface Area | 1163.867 $m^2/g$ |
| Single Point Total Pore Volume at $P/P_o$ = 0.875 | 0.062664 $cm^{2/g}$ |
| Average Pore Diameter (4V/A by BET) | 21.5923 Å |

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An organometallic zeolite which is made of a multiplicity of units, each of which is of the following formula:

$$(X.M)_m$$

wherein

M is a metal ion selected from the group consisting of $Ni^{2+}$, $Sn^{2+}$, $Mg^{2+}$, $Ca^{2+}$, $Fe^{2+}$, $Co^{2+}$, $Mn^{2+}$, and $Ru^{2+}$;

X is a symmetrical porphine which coordinates to a metal ion to form an (X.M) and is substituted with at least two linking groups and optionally with one or more non-linking groups; each linking group being an oxygen-, nitrogen-, or sulfur-containing moiety and having a lone pair of electrons, and each of the non-linking groups, independently, being aryl, heteroaryl, aralkyl, or heteroaralkyl, optionally substituted with alkyl, alkoxy, hydroxyl, hydroxylalkyl, carboxyl, halo, haloalkyl, amino, aminoalkyl, mercapto, mercaptoalkyl, alkylcarbonyloxy, alkyloxycarbonyl, alkylcarbonyl, alkylcarbonylamino, aminocarbonyl, alkylsulfonylamino, aminosulfonyl, dihydroxyboryl, sulfo, or alkylsulfonyl;

m is an integer ranging from 4 to 12; and provided that each $(X.M)_m$ forms a ring-shaped structure with a pore of an interior diameter of 10 to 35 Å and the non-linking group of each X.M, if present, is located inside a pore; the linking group of each X.M coordinates to the metal ion of a neighboring X.M and the metal ion of each X.M further coordinates to a linking group of a neighboring X.M; and each $(X.M)_m$ shares an X.M with each of its neighboring $(X.M)_m$;

or a salt thereof.

2. The organometallic zeolite of claim 1, wherein M is $Co^{2+}$ or $Mn^{2+}$.

3. The organometallic zeolite of claim 1, wherein the symmetrical porphine is substituted with 2–4 linking groups.

4. The organometallic zeolite of claim 3, wherein the porphine is substituted with two linking groups.

5. The organometallic zeolite of claim 4, wherein each of the two linking groups is bonded to the 5-position and the 15-position of the porphine, respectively.

6. The organometallic zeolite of claim 5, wherein the linking group is 4-pyridyl.

7. The organometallic zeolite of claim 6, wherein the porphine is substituted with 1–10 non-linking groups.

8. The organometallic zeolite of claim 7, wherein the porphine is substituted with two non-linking groups.

9. The organometallic zeolite of claim 7, wherein each of the non-linking groups is bonded to the 10-position and the 20-position of the porphine, respectively.

10. The organometallic zeolite of claim 9, wherein the non-linking group is phenyl, subsituted phenyl, 4-pyridyl, or subsituted 4-pyridyl.

11. The organometallic zeolite of claim 10, wherein the non-linking group is 4-pyridyl.

12. The organometallic zeolite of claim 10, wherein the phenyl is substituted with amino, hydroxyl, mercapto, dihydroxyboryl, or carboxyl.

13. The organometallic zeolite of claim 12, wherein the phenyl is substituted with amino or hydroxyl.

14. The organometallic zeolite of claim 13, wherein the phenyl is substituted at the para position.

15. The organometallic zeolite of claim 10, wherein M is $Co^{2+}$ or $Mn^{2+}$.

16. The organometallic zeolite of claim 8, wherein m is 4–8.

17. The organometallic zeolite of claim 16, wherein m is 6.

18. The organometallic zeolite of claim 17, said zeolite is (5,10,15,20-tetra(4-pyridyl)-21H,23H-porphine:$Co^{2+})_6$; (5,10,15,20-tetra(4-pyridyl)-21H,23H-porphine:$Mn^{2+})_6$; (5,15-di(4-pyridyl)-10,20-di(4-aminophenyl)-21H,23H-porphyrin:$Co^{2+})_6$; (5,15-di(4-pyridyl)-10,20-di(4-aminophenyl)-21H,23H-porphyrin:$Mn^{2+})_6$; (5,15-di(4-pyridyl)-10,20-di(4-hydroxyphenyl)-21H,23H-porphyrin:$Co^{2+})_6$; or (5,15-di(4-pyridyl)-10,20-di(4-hydroxyphenyl)-21H,23H-porphyrin:$Mn^{2+})_6$.

* * * * *